US008961404B2

(12) United States Patent
Ito

(10) Patent No.: US 8,961,404 B2
(45) Date of Patent: Feb. 24, 2015

(54) ENDOSCOPE APPARATUS

(75) Inventor: Hiroshi Ito, Hachioji (JP)

(73) Assignee: Olympus Corporation, Tokyo (JP)

( * ) Notice: Subject to any disclaimer, the term of this patent is extended or adjusted under 35 U.S.C. 154(b) by 989 days.

(21) Appl. No.: 12/891,078

(22) Filed: Sep. 27, 2010

(65) Prior Publication Data

US 2011/0082336 A1 Apr. 7, 2011

(30) Foreign Application Priority Data

Oct. 2, 2009 (JP) ................................. 2009-230870

(51) Int. Cl.
*A61B 1/00* (2006.01)
*A61B 1/12* (2006.01)

(52) U.S. Cl.
CPC ......... *A61B 1/00096* (2013.01); *A61B 1/00091* (2013.01); *A61B 1/126* (2013.01)
USPC ............................. 600/176; 600/169; 600/177

(58) Field of Classification Search
USPC ......... 600/160, 169, 156–159, 133, 140, 150, 600/152, 437–444, 463, 466, 467, 470, 600/472; 73/597; 310/327, 334; 333/193, 333/195; 367/155
See application file for complete search history.

(56) References Cited

U.S. PATENT DOCUMENTS

| | | | | |
|---|---|---|---|---|
| 5,980,454 A | * | 11/1999 | Broome | 600/176 |
| 5,995,453 A | * | 11/1999 | Hirata | 367/155 |
| 7,245,193 B2 | * | 7/2007 | Funasaka | 333/193 |
| 7,395,711 B2 | * | 7/2008 | Greenwood | 73/597 |
| 7,867,169 B2 | * | 1/2011 | Webler et al. | 600/463 |
| 7,994,689 B2 | * | 8/2011 | Sawada et al. | 310/334 |
| 8,025,818 B2 | * | 9/2011 | Alkemper et al. | 264/1.21 |
| 2008/0188714 A1 | | 8/2008 | McCaffrey | |
| 2011/0201888 A1 | * | 8/2011 | Verner | 600/160 |

FOREIGN PATENT DOCUMENTS

| | | |
|---|---|---|
| EP | 2 110 070 A1 | 10/2009 |
| JP | 2006-055275 | 3/2006 |

OTHER PUBLICATIONS

Endoscope Apparatus, Yamaguchi Takao, Application #JP 2004-238496, Filing Date Aug. 18, 2004, pp. 1-8.*

(Continued)

*Primary Examiner* — Anhtuan T Nguyen
*Assistant Examiner* — Rajaa El Alami
(74) *Attorney, Agent, or Firm* — Scully, Scott, Murphy & Presser, PC

(57) ABSTRACT

An endoscope apparatus includes a transparent member that is provided at a distal end of an insertion portion of an endoscope and opposed to an image pickup optical system, a transducer that is attached to an inner surface of the transparent member, a diffraction grating that is provided on an outer surface of the transparent member, and converts an ultrasound vibration f from the transducer into a surface acoustic wave φ which propagates on the outer surface of the transparent member, and absorption portions that are provided at an outer peripheral portion of the transparent member, and deflect the propagated surface acoustic wave φ to a surface different from the outer surface to absorb the surface acoustic wave.

5 Claims, 10 Drawing Sheets

(56) References Cited

OTHER PUBLICATIONS

Diffractive Optical Elements in Titanium Oxide for MOEMS Applications, Parashar et al., Institute of Microelectronics and Microsystems 'Institute of Biomedical Imaging, Optics and Engineering, The 12th International Conference on Solid Slate Sensors, Actuators and MicrosystemS. Boston, Jun. 8-12, 2003.*

Extended European Search Report dated Feb. 15, 2011.

* cited by examiner

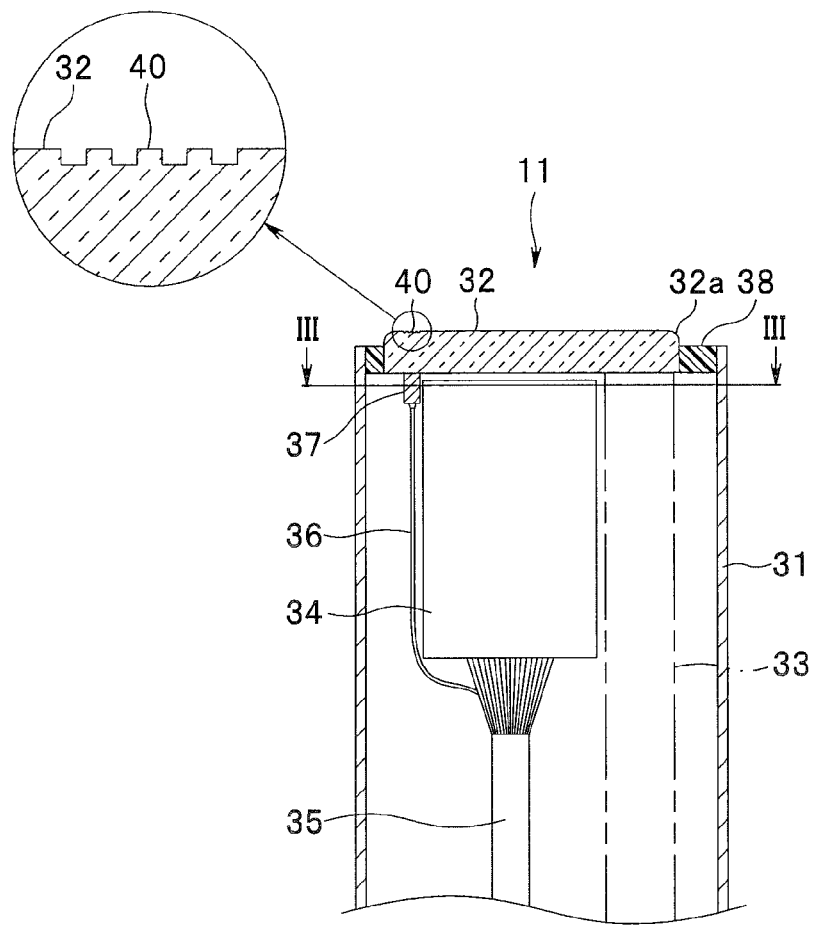
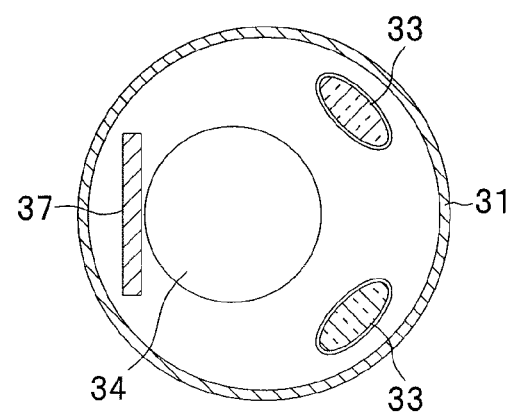

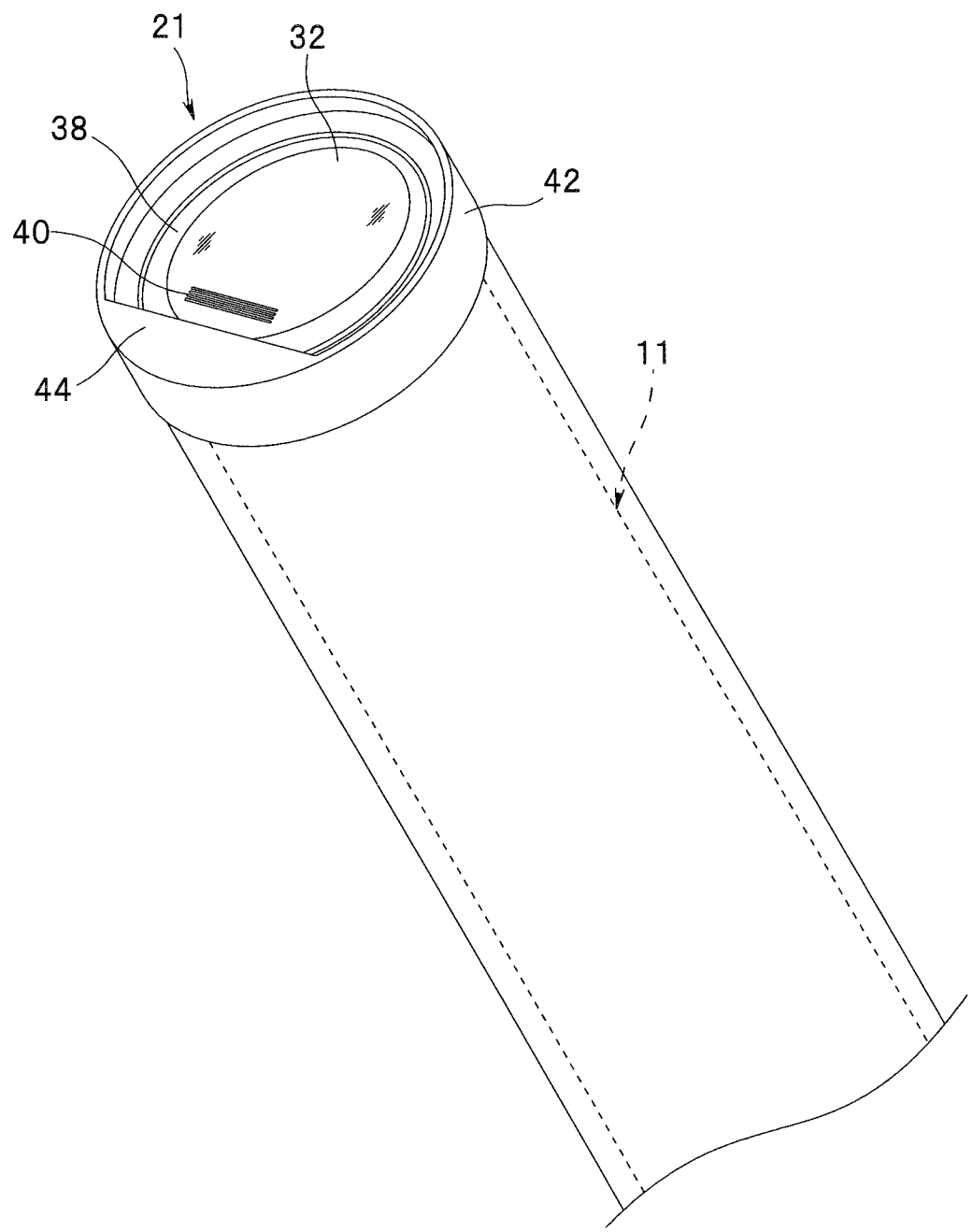

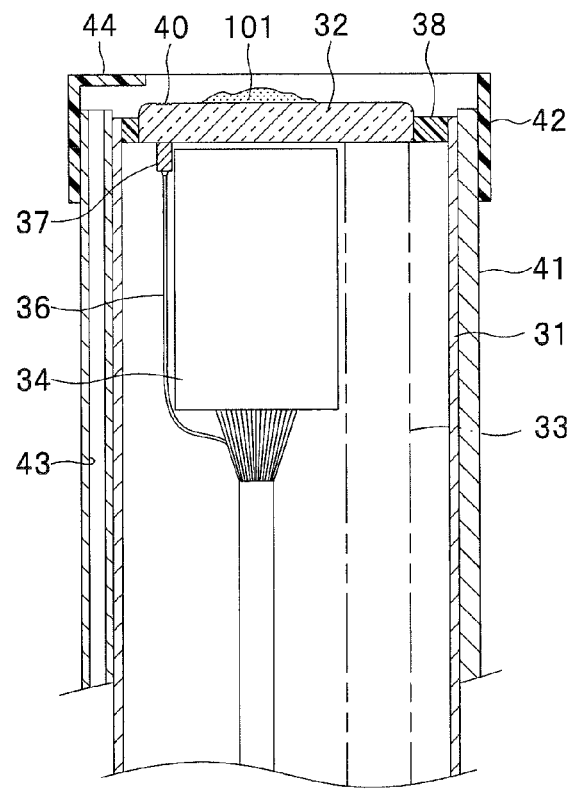
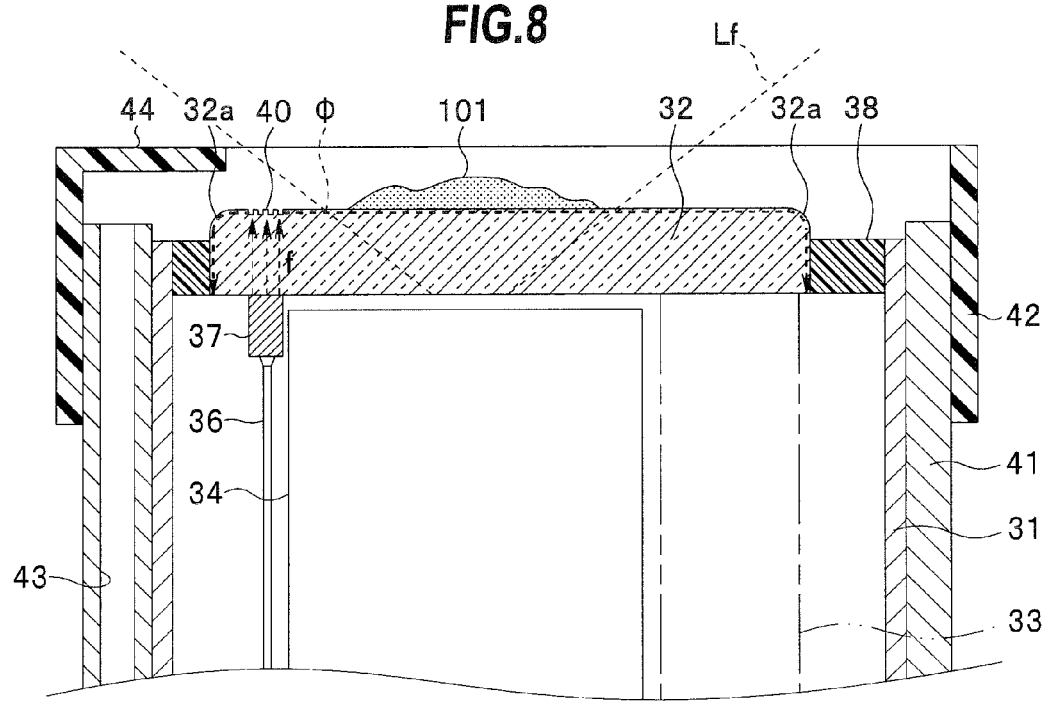

ENDOSCOPE APPARATUS

CROSS REFERENCE TO RELATED APPLICATION

This application claims benefit of Japanese Application No. 2009-230870 filed in Japan on Oct. 2, 2009, the contents of which are incorporated by this reference.

BACKGROUND OF THE INVENTION

1. Field of the Invention

The present invention relates to an endoscope apparatus which enhances observation performance by reliably removing an extraneous matter on an observation window surface.

2. Description of the Related Art

In recent years, with the purpose of performing minimally invasive medical care, surgery using endoscopes has become widespread. In such an endoscopic operation, a challenge is to prevent deterioration of an observation environment due to adherence of contaminations and occurrence of fogging to the observation window placed at an endoscope distal end portion.

In some endoscopes for digestive organs, fogging and contaminations are removed by supply of water to the lenses at the endoscope distal end portions, but in surgical endoscopes, the adhering contaminations are sometimes blood, fats and the like scattered by surgical operations, and the contaminations cannot be removed simply only by water supply in many cases. Further, among the endoscopes for digestive organs, in some transnasal type endoscopes, the distal end portions are thin, and the components are densely arranged. Therefore, removal of the droplets after water supply can be sometimes insufficient.

As countermeasures against the problem, the art disclosed in Japanese Patent Application Laid-Open Publication No. 2006-55275 is known, for example.

In this conventional endoscope apparatus, at a distal end of an inner tube of an insertion portion, a cover glass as an image capturing window is attached to correspond to an objective optical system. A coating layer that is a hydrophilic treatment layer having hydrophilicity of, for example, a photocatalyst (titanium oxide or the like) is formed on an outer surface of the cover glass.

When condensation occurs on the cover glass due to a temperature difference from the ambient environment, the coating layer diffuses the water particles by the hydrophilicity to form a water film in a thin film shape to prevent the surface from being fogged. More specifically, by formation of the water film, a clear field of view which is in the initial state is ensured without causing fogging on the cover glass outer surface. Contaminations such as a body fluid, and droplets by an electric knife not illustrated contact the water film formed on the coating layer of the cover glass, these contaminations adhere to the water film.

Further, the inner tube of the insertion portion is provided with an ultrasound transducer to be capable of transmitting vibration to the cover glass. The ultrasound transducer is subjected to drive control to oscillate to generate ultrasound vibrations, and the ultrasound vibrations are propagated to the cover glass. Here, in the conventional endoscope apparatus, by the action of the ultrasound vibration propagated to the cover glass and the gravity, the water film formed to adhere to the coating layer on the outer surface of the cover glass drops and is removed. At this time, the contamination adhering to the water film is also dropped with the water film, and cleaning of the outer surface of the cover glass is performed. The water film also can be formed by replenishing water onto the coating layer by a water supply nozzle or the like. By the above, the extraneous matters (contaminations, water droplets and a water film) on the outer surface of the cover glass are removed.

SUMMARY OF THE INVENTION

An endoscope apparatus includes a transparent member that is provided at a distal end of an insertion portion of an endoscope and opposed to an image pickup optical system, a transducer that is attached to an inner surface of the transparent member, a diffraction grating that is provided on an outer surface of the transparent member, and converts an ultrasound vibration from the transducer into a surface acoustic wave which propagates on the outer surface of the transparent member, and an absorption portion that is provided at an outer peripheral portion of the transparent member, and deflects the surface acoustic wave to a surface different from the outer surface to absorb the surface acoustic wave.

The above and other objects, features and advantages of the invention will become more clearly understood from the following description referring to the accompanying drawings.

BRIEF DESCRIPTION OF THE DRAWINGS

FIG. 2A is a sectional view showing a configuration of a distal end portion of a rigid endoscope, and FIG. 2B is an enlarged view of a part of the distal end portion of the rigid endoscope, according to the first embodiment of the present invention;

FIG. 3 is a sectional view cut along the III-III line of FIG. 2A according to the first embodiment of the present invention;

FIG. 6 is a perspective view of a distal end portion showing a state in which an insertion portion of the rigid endoscope is installed in the water supply sheath by being inserted through the water supply sheath according to the first embodiment of the present invention;

FIG. 7 is a sectional view of the distal end portion showing a state in which the insertion portion of the rigid endoscope is installed in the water supply sheath by being inserted through the water supply sheath, and is a view showing a state in which an extraneous matter adheres to an observation window, according to the first embodiment of the present invention;

FIG. 8 is an enlarged view of the distal end portion showing a state in which the insertion portion of the rigid endoscope of FIG. 7 is installed in the water supply sheath by being inserted through the water supply sheath, according to the first embodiment of the present invention;

DETAILED DESCRIPTION OF THE PREFERRED EMBODIMENTS

Hereinafter, an endoscope apparatus that is the present invention will be described. Note that in the following description, the drawings based on each of the embodiments are schematic, and the relation of the thickness and the width of each portion, the ratio of the thicknesses of the respective portions and the like differ from realities. The portions differing in the relation and the ratio of the sizes of each other may be included among the drawings.

First Embodiment

First, a first embodiment of the present invention will be described based on the drawings. In the following description, a rigid endoscope for performing laparoscopic surgery, for example, will be shown as an example.

Figure 1:
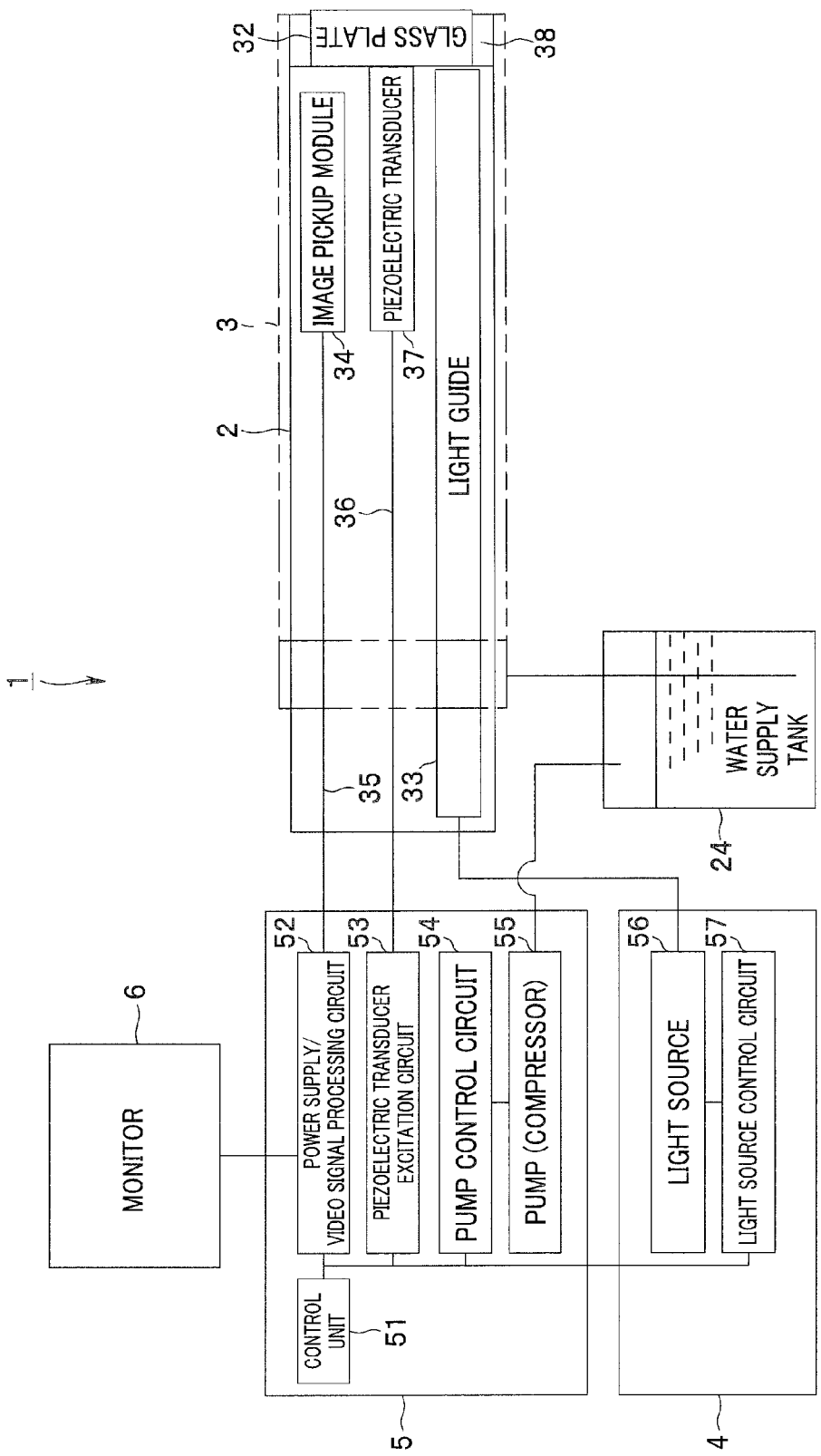
FIG. 1 is a block diagram mainly showing an entire configuration and an electric configuration of an endoscope system according to a first embodiment of the present invention.
Figure 4:
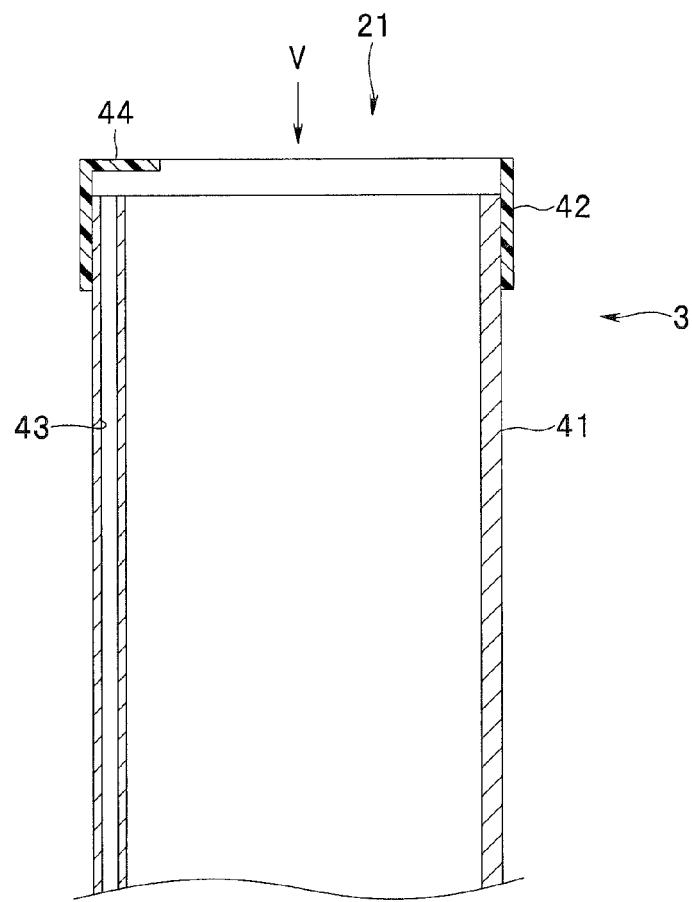
FIG. 4 is a sectional view showing a configuration of a distal end portion of a water supply sheath according to the first embodiment of the present invention.
Figure 5:
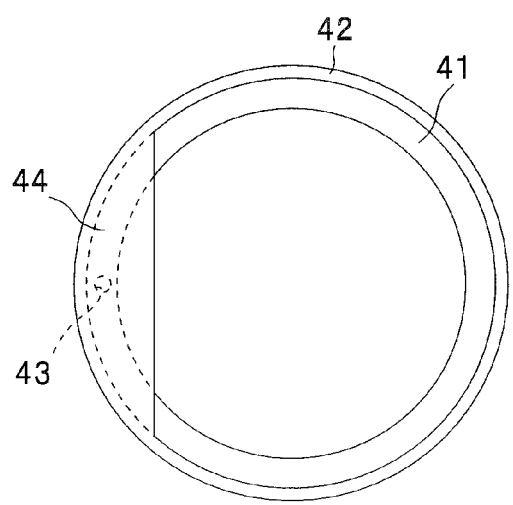
FIG. 5 is a plan view showing a configuration of the water supply sheath in the direction of the arrow V of FIG. 4, according to the first embodiment of the present invention.
Figure 9:
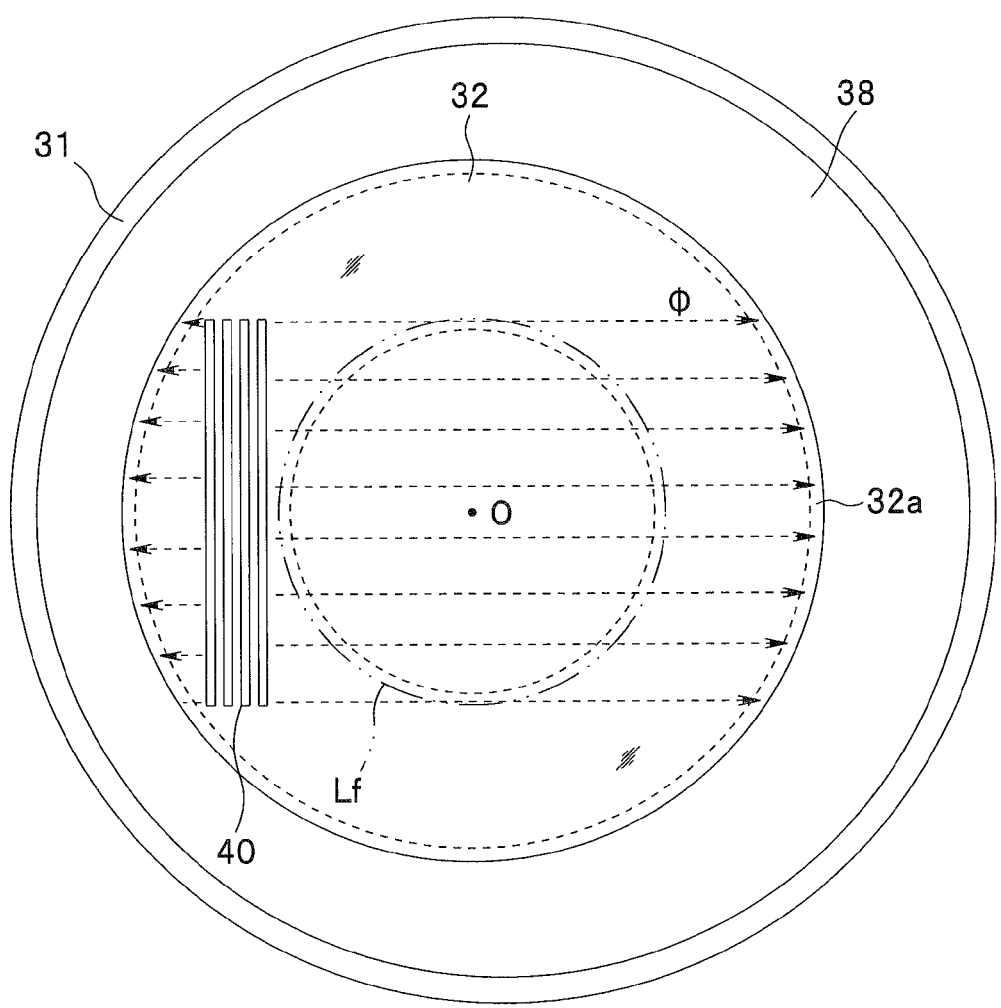
FIG. 9 is a plan view showing a distal end surface of the rigid endoscope for explaining propagation of a surface acoustic wave according to the first embodiment of the present invention.

Further, FIGS. 1 to 9 relate to the first embodiment of the present invention. FIG. 1 is a block diagram mainly showing an entire configuration and an electric configuration of an endoscope system. FIGS. 2A and 2B are sectional views showing a configuration of a distal end portion of the rigid endoscope. FIG. 3 is a sectional view of the distal end portion cut along the III-III line of FIG. 2A. FIG. 4 is a sectional view showing a configuration of a distal end portion of a water supply sheath. FIG. 5 is a plan view showing a configuration of the water supply sheath in the direction of the arrow V of FIG. 4. FIG. 6 is a perspective view of a distal end portion showing a state in which an insertion portion of the rigid endoscope is installed in the water supply sheath by being inserted through the water supply sheath. FIG. 7 is a sectional view of the distal end portion showing the state in which the insertion portion of the rigid endoscope is installed in the water supply sheath by being inserted through the water supply sheath, and is a view showing a state in which an extraneous matter adheres to an observation window. FIG. 8 is an enlarged view of the distal end portion showing the state in which the insertion portion of the rigid endoscope of FIG. 7 is installed in the water supply sheath by being inserted through the water supply sheath. FIG. 9 is a plan view showing a distal end surface of the rigid endoscope for explaining propagation of surface acoustic waves.

As shown in FIG. 1, an endoscope system 1 that is the endoscope apparatus of the present embodiment is mainly configured by a rigid endoscope (hereinafter, simply called an endoscope) 2, a water supply sheath 3 which configures cleaning fluid supply means, in which an insertion portion 11 of the endoscope 2 is installed by being inserted through, a video processor 5, a light source apparatus 4, and a monitor 6.

The endoscope 2 is not illustrated in any of the drawings, since the endoscope has the configuration similar to the conventional configuration. The endoscope 2 is configured by having an operation portion provided connectively to the rigid insertion portion 11 (see FIG. 2A), switches provided at the operation portion, a universal cable which is a composite cable extending from the operation portion, a light source connector placed at an extension end of the universal cable, an electric cable extending from a side portion of the light source connector, and an electric connector placed at an extension end of the electric cable. The light source connector is attachably and detachably connected to the light source apparatus 4. Further, the electric connector is attachably and detachably connected to the video processor 5.

Further, the video processor 5 is electrically connected to the light source apparatus 4 and the monitor 6. The video processor 5 converts the image data picked up by the endoscope 2 into a video signal and displays the image data on the monitor 6. Further, the video processor 5 configures a control apparatus that is control means for receiving operation signals of the switches placed at the operation portion of the endoscope 2, and based on these signals, controlling the light source apparatus 4, feeding air to the water supply tank 24, and performing control to supply a physiological saline solution or the like that is a cleaning solution in the water supply tank 24 to the water supply sheath 3.

Next, an electric configuration of the endoscope system 1 will be mainly described hereinafter based on FIG. 1.

As shown in FIG. 1, the video processor 5 is configured by having a control unit 51 that is a CPU, a power supply/video signal processing circuit 52, a piezoelectric transducer excitation circuit 53, a pump control circuit 54, and a pump 55 that is a compressor.

The control unit 51 is electrically connected to the power supply/video signal processing circuit 52, the piezoelectric transducer excitation circuit 53, and the pump control circuit 54, and controls the respective circuits. Further, the power supply/video signal processing circuit 52 is also electrically connected to the monitor 6, and outputs an endoscope image signal to the monitor 6.

The piezoelectric transducer excitation circuit 53 has the function of vibrating the piezoelectric transducer 37 of the endoscope 2, and variably controls the vibration strength of the piezoelectric transducer 37 by electric energy which is outputted, by control of the control unit 51.

The pump control circuit 54 is electrically connected to the pump 55, and outputs an electric signal for performing drive control of the pump 55 by control of the control unit 51.

The light source apparatus 4 is configured by having a light source 56 such as a halogen lamp, and a light source control circuit 57 which drives the light source 56. The light source control circuit 57 is electrically connected to the control unit 51 of the video processor 5 and is controlled by the control unit 51.

Next, a configuration of a distal end portion of the insertion portion 11 of the endoscope 2 will be described hereinafter based on FIGS. 2A, 2B and 3.

In the insertion portion 11 of the endoscope 2, a fixed support member 38 which configures a part of an absorption portion in the present embodiment is fitted in and fixed to a distal end of a metal tubular member 31 which configures an outer sheath of the insertion portion, as shown in FIGS. 2A, 2B and 3. A substantially disk-shaped glass plate 32 of a transparent member that is an observation window supported and fixed so that a periphery thereof is covered with the fixed support member 38 is joined via an adhesive agent.

An image pickup module 34 including an image pickup optical system, and two illumination light guides 33 in this case are installed inside the tubular member 31. An image forming optical system, a solid image pickup device and a driver chip are incorporated inside the image pickup module 34 configuring the image pickup optical system, though not illustrated in detail, and a communication cable 35 is led out in a direction of a bottom.

Further, on an inner surface (back surface) of the glass plate 32, a rectangular piezoelectric transducer 37 is attached to a position where the piezoelectric transducer does not interfere with the observation field of view, that is, to one region side outward (direction apart from a part of the outer periphery by a predetermined distance in this case) of the image pickup module 34 which is oppositely installed. A wiring 36 is connected to the piezoelectric transducer 37 so that the piezoelectric transducer 37 is electrically driven. More specifically, at the piezoelectric transducer 37, the wiring 36 for supplying a voltage for excitation is led out in the direction of the bottom of the endoscope 2. Further, fixation of the piezoelectric transducer 37 to the glass plate 32 is not limited to fixation by the adhesive agent, but may be fixation by soldering or the like. The piezoelectric transducer 37 is driven at its resonance frequency, or at a frequency in the vicinity of the resonance frequency, and generates ultrasound vibrations inside the glass plate 32.

The glass plate 32 is provided with a diffraction grating 40 in which a plurality of linear groove portions rectangular in section as shown in FIG. 2B are arranged in parallel at a position of the outer surface, which is opposed to the piezoelectric transducer 37 attached to the inner surface (back surface). More specifically, an area of the piezoelectric transducer 37 attached to the inner surface of the glass plate 32 is the same as or larger than an area of the diffraction grating 40 formed on the outer surface of the glass plate 32. Further, a corner portion of an outer surface peripheral portion of the glass plate 32 is formed into a curved surface, and a curved surface portion 32a is formed, which configures a part of the absorption portion that deflects the direction of the surface acoustic waves to the surface different from the outer surface.

An ultrasound vibration f (see FIG. 8) generated from the aforementioned piezoelectric transducer 37 mainly propagates in the direction perpendicular to the attaching surface (inner surface of the glass plate 32) of the piezoelectric transducer 37, and is incident on the above described diffraction grating 40 of the glass plate 32 opposed to the piezoelectric transducer 37. The ultrasound vibration incident on the diffraction grating 40 is converted into a surface acoustic wave $\phi$ (see FIG. 8) propagating on the outer surface of the glass plate 32 by the diffraction grating 40.

In the present embodiment, a grating period which is a structure parameter of the diffraction grating 40 has the value obtained by dividing a velocity of the surface acoustic wave $\phi$ propagating on the glass plate 32 by a frequency of the ultrasound vibration f, and has substantially the same value as a wavelength of the surface acoustic wave $\phi$ irradiated from the diffraction grating 40. Further, a depth of the groove of the diffraction grating 40 is set to about one-tenth of the grating period.

The aforementioned curved surface portion 32a is formed at corner portions of an entire periphery of the glass plate 32 for prevention of reduction in productivity, but as a matter of course, the curved surface portion 32a may be formed in only the outer peripheral corner portion region of the glass plate 32 which the surface acoustic wave $\phi$, into which the ultrasound vibration generated by the piezoelectric transducer 37 is converted by the diffraction grating 40, reaches by propagating.

Further, the components of the endoscope 2 are sealed by the tubular member 31 and the glass plate 32 jointed to the tubular member 31 via the fixed support member 38 so as to be of the structure which can withstand sterilization treatment by high-pressure steam.

Further, in the present embodiment, the inner surface of the glass plate 32, which is opposed to the image pickup optical system of the image pickup module 34 is formed into a planar shape, but a part of the surface opposed to the image pickup optical system may be in a convex or concave shape to configure a part of the image pickup optical system.

Further, the light guide 33 of the present embodiment is provided to extend to the universal cable, and the light guide 33 is terminated at the light source connector. The communication cable 35 and the wiring 36 are connected to the electric connector through the electric cable.

More specifically, the endoscope 2 is configured such that through the universal cable and the electric cable, the light guide 33 is connected to the light source 56 of the light source apparatus 4 including the light source control circuit 57, the communication cable 35 led out from the image pickup module 34 is connected to the power supply/video signal processing circuit 52 of the video processor 5, and the wiring 36 led out from the piezoelectric transducer 37 is connected to the piezoelectric transducer excitation circuit 53 configuring excitation means of the video processor 5, respectively.

Next, the water supply sheath 3 will be described hereinafter based on FIGS. 4 and 5.

The water supply sheath 3 is configured by having a covering tube 21 including a distal end member, a connecting portion not illustrated which is provided to connect to a base end of the covering tube 21, and a water supply tube not illustrated which is extended out from a side portion of the connecting portion. An extension end of the water supply tube is connected to the water supply tank 24. One end of an air supply tube the other end of which is connected to an air supply connector (both are not illustrated) of the video processor 5 is connected to the water supply tank 24.

The covering tube 21 of the water supply sheath 3 is configured by having a tube main body 41, and a substantially cylindrical distal end member 42 fitted on a distal end of the tube main body 41. One water supply passage 43 circular in section for supplying water is formed in a part of a thick portion of the tube main body 41. The water supply passage 43 is placed up to the connecting portion, and connects with the water supply tube through the connecting portion.

The distal end member 42 has an eave portion 44 that is a plate body along an opening end surface at the position opposed to the water supply passage 43 of the tube main body 41.

In the water supply sheath 3 thus configured, the water supply passage 43 is connected with the water supply tank 24 through the water supply tube. The physiological saline solution or the like that is a cleaning solution in the water supply tank 24 is pumped into the water supply passage 43 to flow to the endoscope distal end portion by the pressure in the water supply tank 24 being increased by the air from the pump 55 controlled by the pump control circuit 54.

The endoscope system 1 of the present embodiment described above is used in, for example, laparoscopic surgery, with the insertion portion 11 of the endoscope 2 being installed in the covering tube 21 of the water supply sheath 3 by being inserted through the covering tube 21, as shown in FIG. 6.

When a contamination 101 such as blood and a fat adheres to the outer surface of the glass plate 32 in the endoscope system 1 during an operation as shown in FIG. 7, a user who is a doctor operates a remote switch among the switches provided at the operation portion of the endoscope 2. Subsequently, in response to the control signal by the switch operation, an excitation signal is supplied to the piezoelectric transducer 37 from the piezoelectric transducer excitation circuit 53 of the video processor 5, and the ultrasound vibration f is generated in the glass plate 32.

Prior to this, by operation of the above described switches, the cleaning solution is supplied to the outer surface of the glass plate 32 from the water supply sheath 3. More specifically, air is supplied into the water supply tank 24 from the pump 55 which is a compressor, and the cleaning solution in the water supply tank 24 is supplied to the water supply sheath 3. The cleaning water spouts from the distal end of the tube main body 41 through the water supply passage 43 formed in the tube main body 41 of the water supply sheath 3, and hits against the eave portion 44, and flows out along the substantially entire outer surface of the glass plate 32.

As shown in FIG. 8, the ultrasound vibration f which is generated on the vibration surface that is the inner surface (back surface) of the glass plate 32 where the piezoelectric transducer 37 is attached propagates in substantially the vertical direction inside the glass plate 32. The ultrasound vibration f reaches the diffraction grating 40, and is converted into the surface acoustic wave which propagates on the outer surface of the glass plate 32 by the diffraction grating 40, and propagates as the surface acoustic wave $\phi$ rectilinearly in a lateral direction on the outer surface of the glass plate 32 toward a center side (an shooting optical axis O condensed by the image pickup optical system of the image pickup module 34) of the glass plate 32, and toward an outer peripheral portion at an opposite side to the center side with the diffraction grating 40 therebetween. The direction of the grating vector that specifies the traveling direction of the surface acoustic wave $\phi$ which is generated by the diffraction grating 40 is defined as the direction of the periodicity of the diffraction grating 40. In this case, the diffraction grating 40 has the configuration in which linear groove portions are installed in parallel, and therefore, the surface acoustic wave $\phi$ is propagated in the two traveling directions opposite from each other with the diffraction grating 40 therebetween in the direction orthogonal to these groove portions.

If the diffraction grating 40 is not provided at the glass plate 32, the ultrasound vibration f repeatedly reflects between the plane of the above described piezoelectric transducer 37 and the outer surface of the glass plate 32 opposed to the plane of the piezoelectric transducer 37 since the directivity of the ultrasound vibration f is high, and the vibration propagates favorably in the opposed portions, but the ultrasound vibration f is not favorably propagated to the other region of the glass plate 32, which is away from the piezoelectric transducer 37.

In contrast with this, when the diffraction grating 40 is provided on the outer surface of the glass plate 32 as in the present embodiment, the ultrasound vibration f directly traveling from the piezoelectric transducer 37 is converted into the rectilinear surface acoustic wave $\phi$ and is propagated toward the direction of the center (the direction in which the shooting optical axis O passes) of the observation field of view region Lf (the two-dot chain line in FIG. 9) of the image pickup module 34 in the glass plate 32 by the diffraction grating 40.

In other words, as shown in FIG. 9, the surface acoustic wave $\phi$ is irradiated in the direction perpendicular to the arrangement direction of the groove portions of the diffraction grating 40. The surface acoustic wave $\phi$ which is propagated in the direction of the center of the glass plate 32 reaches and further passes the observation field of view region Lf portion on the outer surface of the glass plate 32. Subsequently, the surface acoustic wave $\phi$ pushes out and removes the contamination 101 such as blood which adheres to the observation field of view region Lf in the propagation direction with supply of the cleaning solution. The surface acoustic wave $\phi$ propagates while gathering the vibrations on the surface of the glass plate 32, and therefore, can remove the contamination by efficiently transmitting the vibrations to the contamination 101 adhering to the outer surface of the glass plate 32.

More specifically, when the generated ultrasound vibration f is incident on the diffraction grating 40, the ultrasound vibration f is converted into the surface acoustic wave $\phi$ toward the direction of the shooting optical axis O. By the diffraction grating 40, even the high-frequency ultrasound vibration f with high directivity can be efficiently propagated as the surface acoustic wave $\phi$ in the direction of the center (the direction in which the shooting optical axis O passes) of the glass plate 32. The contamination 101 adhering to the outer surface is mixed with the cleaning solution, a part of the contamination 101 is atomized, and a part of the contamination 101 is forced to flow with the cleaning solution, whereby the contamination 101 can be efficiently and reliably removed over the substantially entire surface of the observation field of view region Lf in the glass plate 32.

Further, the surface acoustic wave $\phi$ which reaches the outer peripheral portion that is an outline portion forming a contour of the outer surface of the glass plate 32 is propagated along an outer peripheral surface to be a side surface of the glass plate 32 by the curved surface portion 32a. The curved surface portion 32a of the present embodiment is chamfered with a radius of curvature larger than the wavelength of the reflected surface acoustic wave $\phi$ so as not to reflect the surface acoustic wave $\phi$ to the outer surface of the glass plate 32.

The surface acoustic wave $\phi$ propagated to the side peripheral surface of the glass plate 32 is absorbed by the fixed support member 38 to be the absorption portion which holds and fixes the outer periphery of the glass plate 32. Further, the surface acoustic wave $\phi$ which propagates in the direction opposite from the observation field of view region Lf of the glass plate 32 from the diffraction grating 40 is similarly propagated to the side peripheral surface of the glass plate 32 along the curved surface portion 32a, and is absorbed by the fixed support member 38 at the outer peripheral portion of the glass plate 32.

When the curved surface portion 32a which restricts reflection of the surface acoustic wave is not formed at the outer peripheral portion of the glass plate 32, or even when the curved surface portion 32a is formed at the glass plate 32, but if the fixed support member 38 is not provided, the surface acoustic wave $\phi$ traveling toward the observation field of view region Lf from the diffraction grating 40, and the surface acoustic wave $\phi$ which is reflected at the outer periphery of the glass plate 32 or the outer peripheral inner surface and travels toward the observation field of view region Lf, and is in a relatively different direction (in a substantially opposite direction different from each other) exist on the outer surface of the glass plate 32 at the same time. As a result, the vibrations by the surface acoustic waves φ in the opposite directions from each other simultaneously act on the contamination 101 adhering to the outer surface of the glass plate 32, forces in the opposite directions from each other act on the contamination 101, and the ability to remove the contamination 101 is likely to be reduced significantly.

In the present embodiment, the curved surface portion 32a which propagates the surface acoustic wave φ propagating on the outer surface of the glass plate 32 to the side peripheral surface of the glass plate 32 is formed at the outer peripheral portion at the outer surface side of the glass plate 32, and the fixed support member 38 to be the absorption portion which absorbs the surface acoustic wave φ is provided at the outer periphery of the glass plate 32, whereby the surface acoustic wave acts onto the contamination 101 in one direction, and the contamination can be efficiently removed.

Further, the present embodiment has an advantage of having no need to provide the absorption member for absorbing the surface acoustic wave φ at the outer surface of the distal end of the endoscope insertion portion which is in contact with the inside of a human body, and is exposed to a chemical at the time of sterilization.

As described above, in the endoscope system 1 of the present embodiment, the ultrasound vibration f of the piezoelectric transducer 37 is efficiently propagated in the direction of the center of the glass plate 32, in other words, in the direction of the center of the observation field of view region Lf of the image pickup module 34, and the contamination 101 on the outer surface of the glass plate 32 opposed to the image pickup module 34 of the endoscope 2, especially, in the observation field of view region Lf can be efficiently removed.

Especially because the grating interval (grating period) is set as substantially the value obtained by dividing the velocity of the surface acoustic wave propagating on the surface of the glass plate 32 by the frequency of the ultrasound vibration f incident on the diffraction grating 40, and therefore, the ultrasound vibration f incident on the diffraction grating can be mode-converted into the surface acoustic wave propagating on the outer surface of the glass plate 32. Since the surface acoustic wave φ propagates while its vibrations concentrated on the surface of the glass plate 32, the vibration is efficiently transmitted to the contamination 101 adhering to the outer surface of the glass plate 32, and the contamination can be removed.

Second Embodiment

Figure 10:
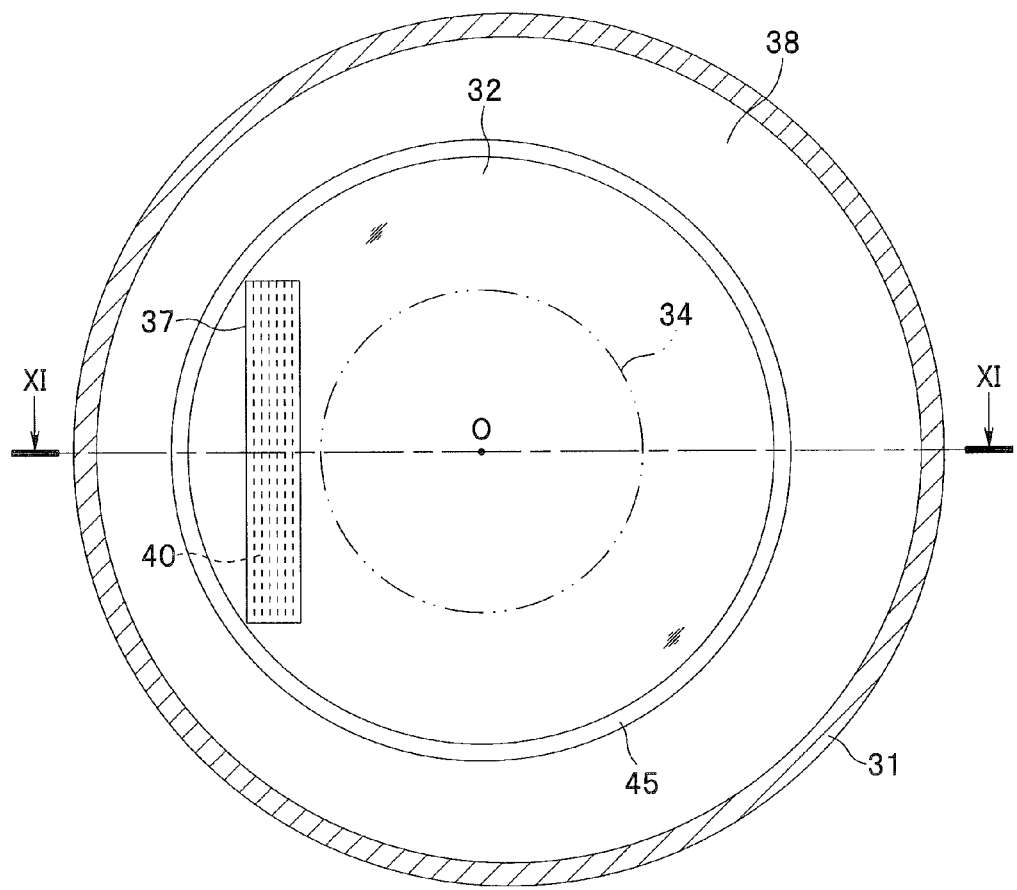
FIG. 10 is a sectional view of an insertion portion of a rigid endoscope with a glass plate seen from an inner surface direction, according to a second embodiment of the present invention.
Figure 11:
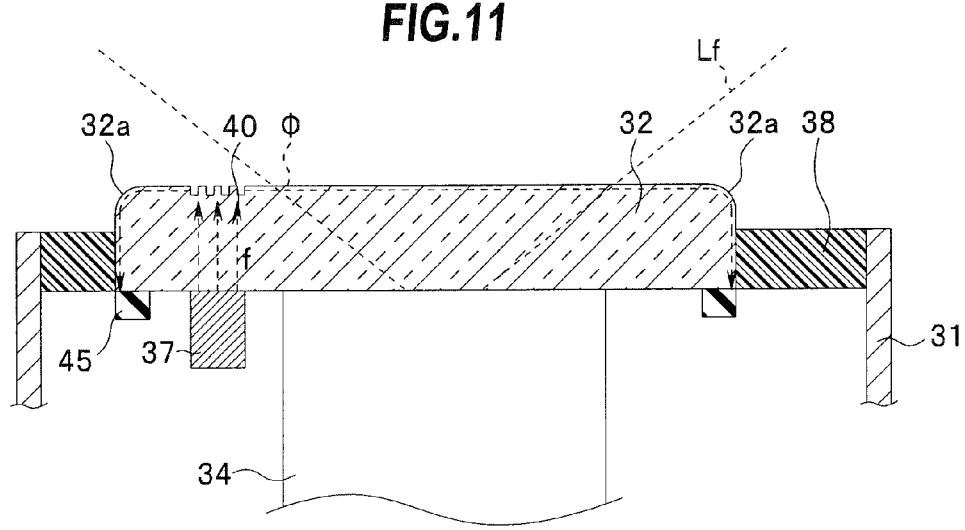
FIG. 11 is a sectional view of a distal end portion cut along the line XI-XI of FIG. 10 according to the second embodiment of the present invention.

Next, a second embodiment of the endoscope system 1 of the present invention will be described in detail hereinafter based on FIGS. 10 and 11. FIGS. 10 and 11 relate to the second embodiment of the present invention. FIG. 10 is a sectional view of an insertion portion of a rigid endoscope with a glass plate seen from an inner surface direction, and FIG. 11 is a sectional view of a distal end portion cut along the XI-XI line of FIG. 10.

In the description of the present embodiment, the components described in the first embodiment will be assigned with the same reference numerals and characters, and the description of the components and the operations will be omitted. Further, the configuration of the present embodiment which will be described hereinafter is also applicable to the endoscope 2 of the first embodiment as a matter of course.

In the present embodiment, the glass plate 32 is provided with a ring-shaped absorption member 45 at an outer peripheral edge portion at the inner surface side. The absorption member 45 is formed of an elastic material such as rubber in order to absorb the surface acoustic wave φ propagating to a side peripheral surface of the glass plate 32 reliably at an inner surface edge side of the glass plate 32 to prevent the surface acoustic wave from reflecting.

For example, when the thickness of the glass plate 32 is small, the wall thickness of the fixed support member 38 has to be made small, so that the contact area with the glass plate 32 becomes small. In this case, the fixed support member 38 sometimes cannot completely absorb the surface acoustic wave φ propagated to the side peripheral surface of the glass plate 32. When the surface acoustic wave φ cannot be absorbed at the side surface of the glass plate 32, the surface acoustic wave φ is reflected at the inner surface of the glass plate 32, and the reflected surface acoustic wave φ propagates to the outer surface from the side peripheral surface of the glass plate 32 via the curved surface portion 32a, which is the route opposite from the incident (propagation) route.

Therefore, in the present embodiment, in addition to the effect of the aforementioned first embodiment, by providing the absorption member 45 at the inner surface edge side portion of the glass plate 32, the surface acoustic wave which cannot be absorbed completely by the fixed support member 38 at the side peripheral surface of the glass plate 32 is absorbed by the absorption member 45, and reflection of the surface acoustic wave φ in the direction opposite from the incident (propagation) route to the outer peripheral portion of the glass plate 32 can be reliably restricted.

Third Embodiment

Figure 12:
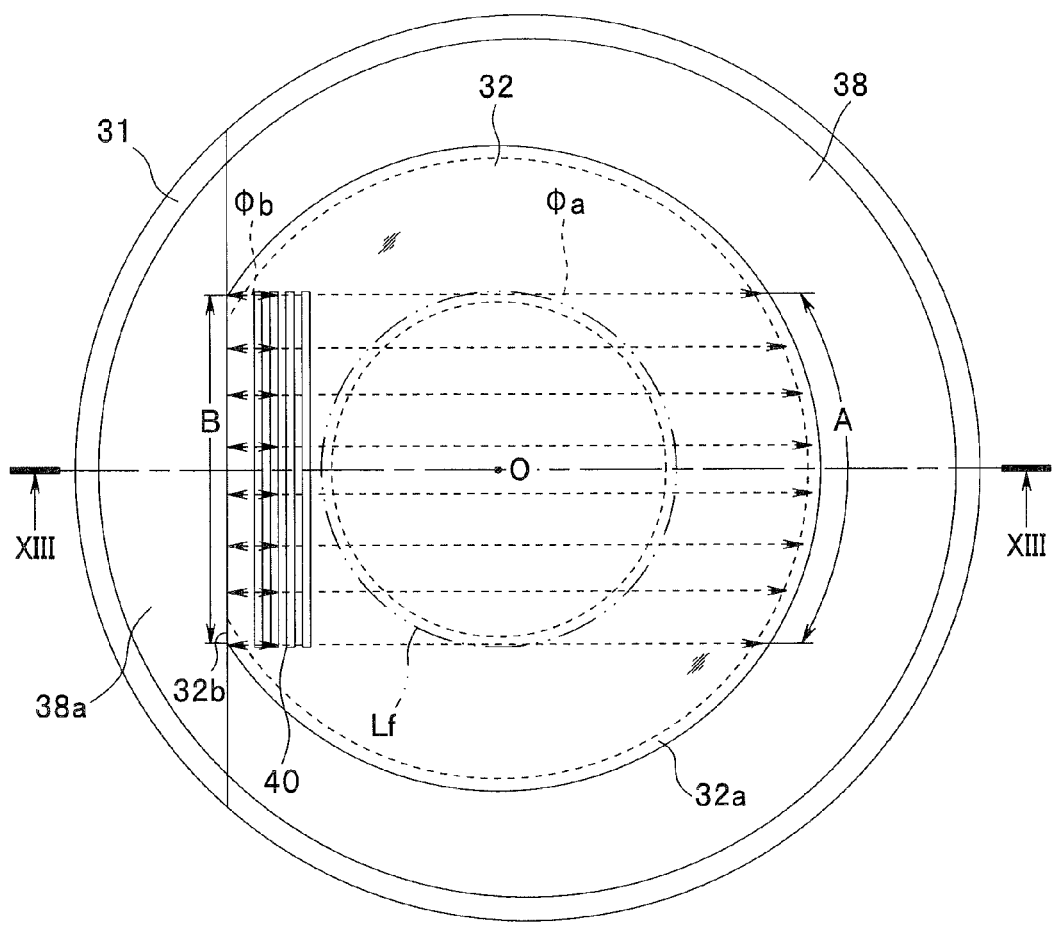
FIG. 12 is a plan view showing a distal end surface of a rigid endoscope for explaining propagation of a surface acoustic wave according to a third embodiment of the present invention.
Figure 13:
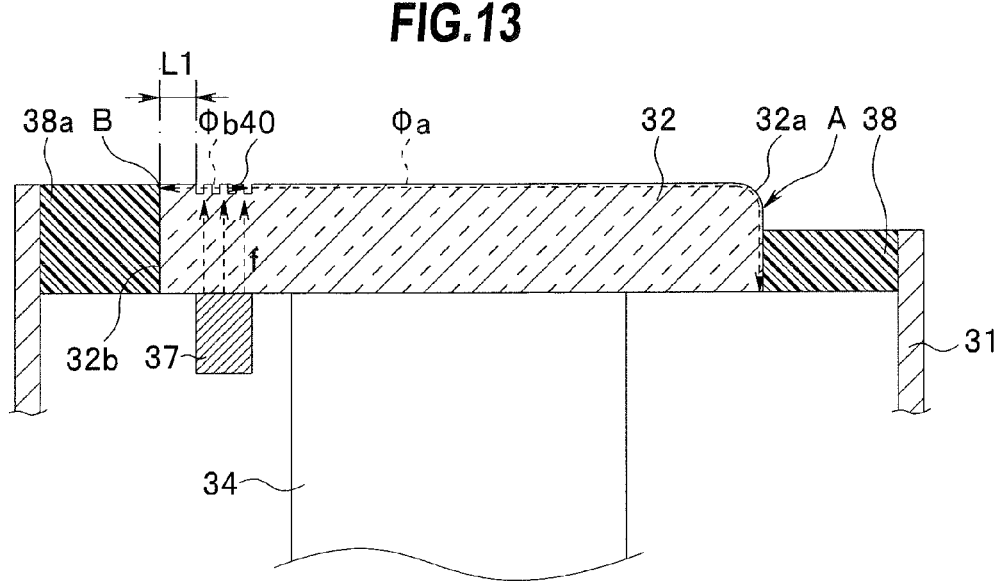
FIG. 13 is a sectional view of a distal end portion cut along the XIII-XIII line of FIG. 12 according to the third embodiment of the present invention.
Figure 14:
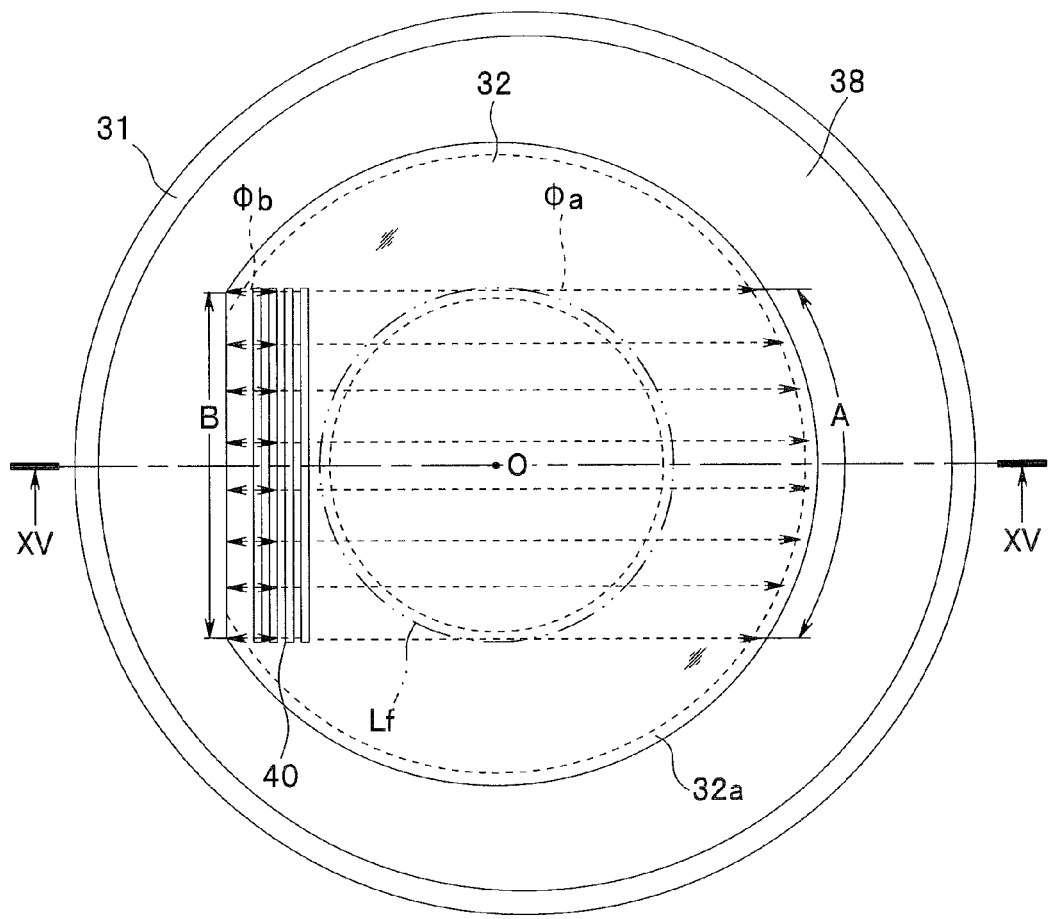
FIG. 14 shows a first modified example, and is a plan view showing a distal end surface of a rigid endoscope for explaining propagation of a surface acoustic wave, according to the third embodiment of the present invention.
Figure 15:
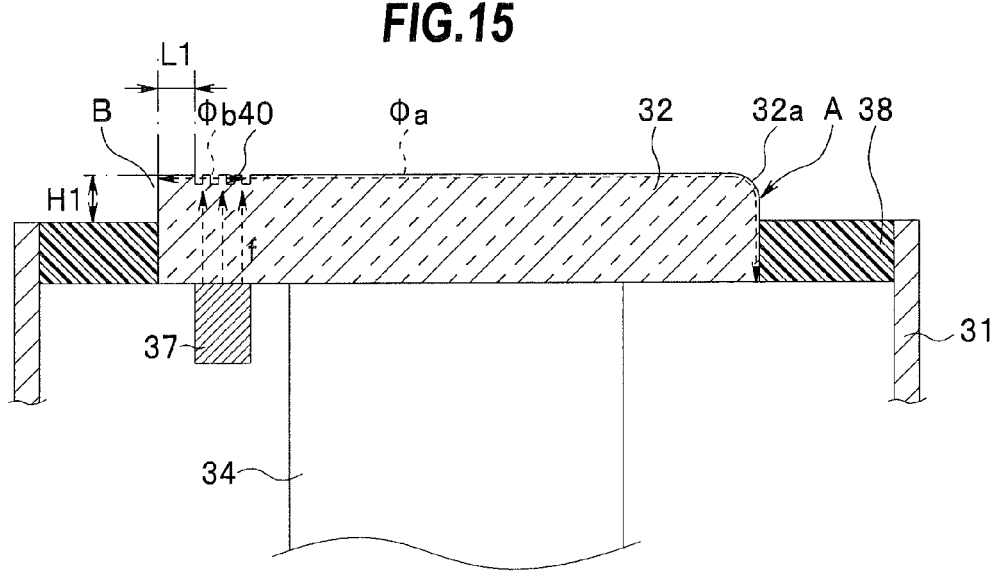
FIG. 15 is a sectional view of a distal end portion cut along the XV-XV line of FIG. 14 according to the third embodiment of the present invention.
Figure 16:
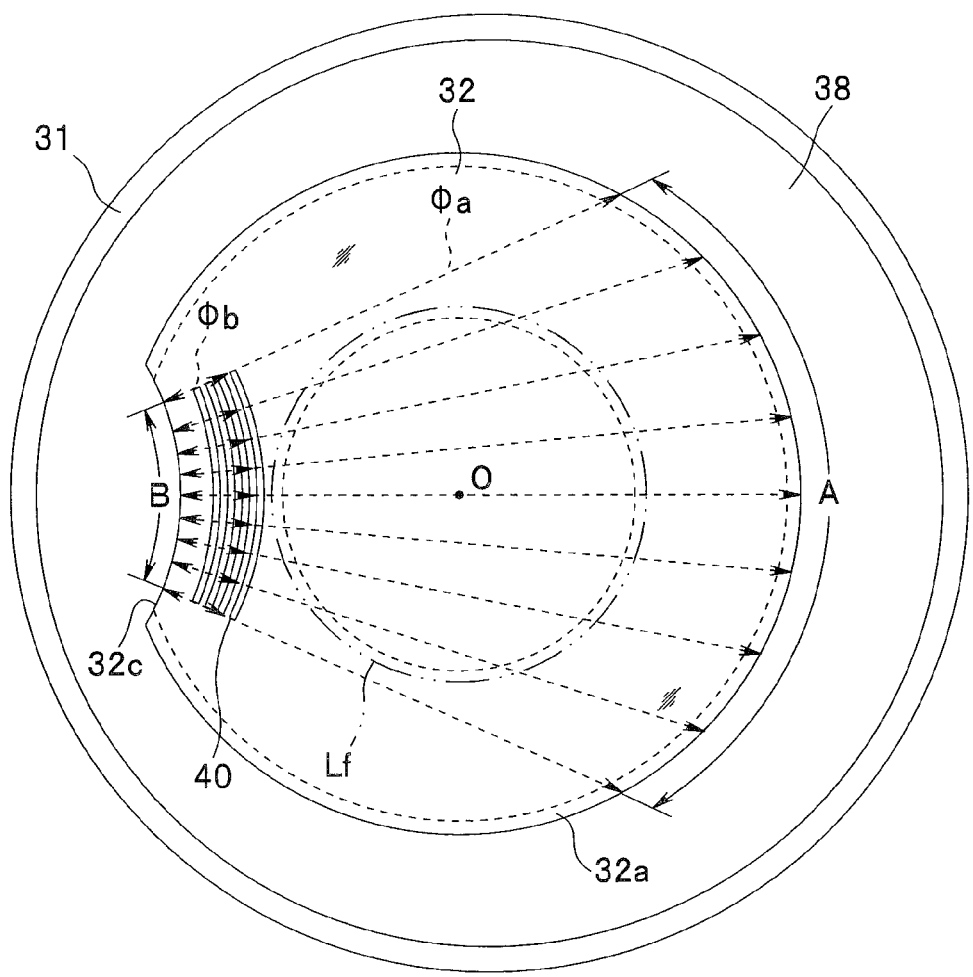
FIG. 16 shows a second modified example, and is a plan view showing a distal end surface of the rigid endoscope for explaining propagation of a surface acoustic wave, according to the third embodiment of the present invention.

Next, a third embodiment of the endoscope system 1 of the present invention will be described in detail hereinafter based on FIGS. 12 to 16. FIGS. 12 to 16 relate to a third embodiment of the present invention. FIG. 12 is a plan view showing a distal end surface of a rigid endoscope for explaining propagation of a surface acoustic wave. FIG. 13 is a sectional view of a distal end portion cut along the XIII-XIII line of FIG. 12. FIG. 14 shows a first modified example, and is a plan view showing a distal end surface of the rigid endoscope for explaining propagation of the surface acoustic wave. FIG. 15 is a sectional view of a distal end portion cut along the XV-XV line of FIG. 14. FIG. 16 shows a second modified example, and is a plan view showing a distal end surface of the rigid endoscope for explaining propagation of the surface acoustic wave.

In the description of the present embodiment, the components described in the first embodiment will be assigned with the same reference numerals and characters, and the description of the components and the operations will be omitted. A configuration of the present embodiment which will be described hereinafter is also applicable to the endoscopes 2 of the first and the second embodiments as a matter of course.

As shown in FIGS. 12 and 13, in the glass plate 32 of the present embodiment, an outer peripheral portion at the side opposite from the observation field of view region Lf with the diffraction grating 40 as a border is parallel with the longitudinal direction of the diffraction grating 40, and a plane portion 32b which is a chamfered portion configuring a reflection surface linearly cut off in the perpendicular direction to the outer surface and the inner surface is formed. A length of the plane portion 32b parallel with the diffraction grating 40 is equal to or larger than the longitudinal length of the groove portion of the diffraction grating 40, and the plane portion 32b is formed at a position separated from the end portion of the diffraction grating 40 by a predetermined distance L1, that is, at a position which the surface acoustic wave φ reaches after covering the predetermined distance L1, and includes a reflection region which reflects the surface acoustic wave φ in the present embodiment.

In the fixed support member 38 which fixes the glass plate 32 at the distal end of the insertion portion 11, a step portion 38a is formed, which is in surface contact with the entire surface of the plane portion 32b of the glass plate 32 and fixes the glass plate 32 via an adhesive agent or the like. More specifically, the step portion 38a has substantially the same thickness as a thickness dimension of the glass plate 32, and is in surface contact with the plane portion 32b of the glass plate 32.

In the present embodiment, regions, where the surface acoustic waves φ propagating on the outer surface of the glass plate 32 reaches the outline end portion (the outer peripheral portion, or the plane portion 32b) which is an outline portion forming a contour of the outer surface of the glass plate 32, are set as regions A and B. When the shape of the groove portions of the diffraction grating 40 is rectilinear, the direction of the grating vector which is the direction in which the surface acoustic wave φ propagates is the direction perpendicular to the longitudinal direction of the groove portion of the diffraction grating 40.

In this case, the outer peripheral portion of the glass plate 32, which a surface acoustic wave φa propagating on the outer surface of the glass plate 32 to the observation field of view region Lf side reaches, and which deflects the surface acoustic wave φa to the side peripheral surface by the curved surface portion 32a, is set as the first region A. The first region A corresponds to the curved surface 32a configuring the absorption portion which deflects and absorbs the surface acoustic wave φa, and the side peripheral surface fixedly supported by the fixed support member 38, in this case, in order to restrict reflection of the surface acoustic wave φa. More specifically, the absorption region including the first region A is configured to include the absorption portion and absorb the surface acoustic wave φa deflected at the curved surface portion 32a of the glass plate 32 by the side peripheral surface, as in each of the aforementioned embodiments.

In other words, the first region A is an arc-shaped region between two points on the outer peripheral portion of the glass plate 32, at which two straight lines arrive, which are drawn to the observation field of view region Lf side from two points at both end portions in the longitudinal direction of the groove portion of the diffraction grating 40, which is formed at the observation field of view region Lf side, and are parallel with the grating vector in the direction orthogonal to the longitudinal direction of the groove portion. The surface acoustic wave φa irradiated to the observation field of view region Lf side from the diffraction grating 40 propagates rectilinearly in parallel with the above described grating vector, and therefore, reaches only the first region A of the outer peripheral portion of the glass plate 32. The surface acoustic wave φa which reaches the first region A is absorbed in the absorption region including the absorption portion without being reflected.

Meanwhile, a region in the plane portion 32b at which a surface acoustic wave φb arrives after propagating on the outer surface of the glass plate 32 at the side opposite from the observation field of view region Lf side, is set as the second region B. The second region B configures a reflection portion at which the surface acoustic wave φb is reflected by the plane portion 32b. More specifically, in the reflection region including the second region B, the plane portion 32b of the glass plate 32 is a plane substantially perpendicular (vertical) to the outer surface, that is, the sectional shape of the plane portion 32b is substantially 90 degrees (the angle formed by the outer surface and the plane portion 32b is substantially 90 degrees), and therefore, has the configuration such that the surface acoustic wave φb which reaches and is incident on the plane portion 32b is reflected.

In other words, the surface acoustic wave φb is also irradiated in the direction opposite from the direction of the observation field of view region Lf from the diffraction grating 40. In this case, the second region B is a rectilinear region between two points on the plane portion 32b of the glass place 32, at which two straight lines arrives, which are drawn from two points at both end portions in the longitudinal direction of the groove portion of the diffraction grating 40, which is formed at the side opposite from the observation field of view region Lf side to the side opposite from the observation field of view region Lf side, and are parallel with the grating vector in the direction orthogonal to the longitudinal direction of the groove portion. The surface acoustic wave φb, which is irradiated to the side opposite from the observation field of view region Lf side from the diffraction grating 40, rectilinearly propagates parallel with the grating vector as described above, and therefore, the surface acoustic wave φb reaches only the second region B of the outer peripheral portion of the glass plate 32. The surface acoustic wave φb which reaches the second region B is reflected at the reflection region by the plane portion 32b without being absorbed.

When seen from the top surface of the glass plate 32, the outline of the glass plate 32 including the plane portion 32b is desirably in a shape parallel with the diffraction grating 40 in the second region B. That is to say, the straight line drawn to be parallel with the aforementioned grating vector from an arbitrary point of the diffraction grating 40 is orthogonal to the plane portion 32b of the glass plate 32 in the second region B, and the distance between the diffraction grating 40 and the plane portion 32b of the glass plate 32 is desirably constant.

Further, the predetermined distance L1 between the diffraction grating 40 and the second region B is desirably the integral multiple of one half of the grating period of the diffraction grating 40 (grating period×½×n, n=integer). By such a configuration, the surface acoustic wave φb which is incident on the second region B is reflected in the opposite direction at 180 degrees with respect to the incident direction, and the reflected wave (surface acoustic wave φb) from the plane portion 32b of the glass plate 32 including the reflection region, and the surface acoustic wave φa which directly propagates to the observation field of view region Lf side from the diffraction grating 40 are superimposed on each other to intensify the amplitudes. Therefore, the reflected wave (surface acoustic wave φb) from the plane portion 32b also contributes to removal of the contaminations.

From the above description, in the present embodiment, in addition to the effect of the aforementioned first embodiment, vibrations are more efficiently transmitted to the contamination 101 adhering to the outer surface of the glass plate 32, and the contamination can be reliably removed.

First Modified Example

Next, based on FIGS. 14 and 15, a first modified example of the present embodiment will be described.

In the present modified example, as shown in FIGS. 14 and 15, in the plane portion 32b including the reflection region of the glass plate 32, the portion which is fixed by surface contact with the fixed support member 38 is configured to be located at a position lowered to the inner surface side by a predetermined height (length) H1 from a wall thickness of the glass plate 32 (thickness dimension from the outer surface to the inner surface). More specifically, the fixed support member 38 does not have the aforementioned step portion 38a formed thereon, includes a wall thickness (thickness dimension) smaller than the wall thickness of the glass plate 32, is in surface contact with and fixed to the plane portion 32b which is the reflection surface, and fixedly supports the glass plate 32. Further, the above described predetermined height H1 is set to be a length (height) of at least one wavelength of the surface acoustic wave φb from the outer surface of the glass plate 32.

The wavelengths of the surface acoustic waves φa and φb are each defined by the vibration frequency of the piezoelectric transducer 37 and the sound velocity of the surface acoustic wave propagating on the glass plate 32. For example, when the vibration frequency of the piezoelectric transducer 37 is 40 MHz, the sound velocity of the surface acoustic waves φa and φb propagating on the outer surface determined by the material of the standard glass plate 32 to be the cover glass is about 3400 m/s, and therefore, the grating period of the diffraction grating 40 is set at about 85 μm. The wavelengths of the surface acoustic waves φa and φb correspond to the grating period, and therefore, the above described predetermined height H1 is 85 μm or more.

Further, 90% or more of the vibration energy of the surface acoustic wave φb concentrates within the depth of about one wavelength from the outer surface of the glass plate 32 on which the surface acoustic wave φa propagates. Therefore, the portion corresponding to one wavelength from the outer surface of the glass plate 32 is not used for fixation of the fixed support member 38 and the plane portion 32b, but is brought into the state in contact with air, whereby reduction in vibration energy can be prevented by increasing the reflectivity of the surface acoustic wave φb on the second region B that is the reflection region, and therefore, the efficiency of removal of the contamination 101 by the reflected wave (surface acoustic wave φb) from the second region B can be enhanced.

Second Modified Example

Next, a second modified example of the present embodiment will be described based on FIG. 16.

When the shapes of the groove portions of the diffraction gratings 40 in the present embodiment described above, and each of the embodiments are rectilinear, the directions of the grating vectors are in the directions perpendicular to the longitudinal directions of the groove portions.

In the present modified example, as shown in FIG. 16, the shapes seen from the top surface side, of a plurality of groove portions which configure the diffraction grating 40 and are provided side by side, form curved lines (arc shapes). The diffraction grating 40 is formed into an arc-shaped curved line group like this, the surface acoustic wave φa, which propagates on the outer surface of the glass plate 32 to the observation field of view region Lf side, is irradiated from the diffraction grating 40 so as to be diffused two-dimensionally.

Further, when the shape of the diffraction grating 40 seen from the top surface is in the arc-shaped curved line, an arc surface 32c is provided, which is a chamfered portion configuring a reflection surface formed by cutting a part of the outline of the glass plate 32 in the direction orthogonal to the outer surface, in order that a predetermined distance to the second region B to be the reflection region from the diffraction grating 40 becomes constant.

In the second region B, the fixed support member 38 has a shape projected by being the arc-shaped curved line to be in surface contact with the arc surface 32c. By such a shape, the straight line which is drawn in parallel with the grating vector to the direction opposite from the observation field of view region Lf side from an arbitrary point of the diffraction grating 40 is orthogonal to the arc surface 32c of the glass plate 32 in the second region B. Therefore, the surface acoustic wave φb is reflected in the opposite direction at 180 degrees with respect to the incident direction.

When the shape of the diffraction grating 40 is an arc-shaped curved line, the grating vector is in the direction perpendicular to a tangential line of the curved line of the groove portion. The direction of the grating vector is the direction in which the surface acoustic wave φ propagates, and therefore, the surface acoustic wave φ propagates in the direction perpendicular to the tangential line of the curved line of the groove portion, that is, the surface acoustic wave φa propagating to the observation field of view region Lf side is irradiated from the diffraction grating 40 to be diffused two-dimensionally. As a result, in addition to the effect of the aforementioned present embodiment, the surface acoustic wave can be propagated in the entire observation field of view region Lf of the glass plate 32 even if the configuration is such that the occupied area of the diffraction grating 40 is smaller in the outer surface of the glass plate 32.

The endoscope system 1 of each of the embodiments described above can adopt the configuration in which the configurations of the second and the third embodiments are combined with the first embodiment as the basic configuration.

More specifically, the invention described in each of the embodiments is not limited to its embodiment and modified examples, and other than them, various modifications can be carried out in the range without departing from the gist of the invention in the stage of carrying out the invention. Further, the above described embodiments include inventions at various stages, and various inventions can be extracted by proper combination in a plurality of components which are disclosed.

For example, even when some components are deleted from all the components shown in the embodiments, if the described problem can be solved and the described effect can be obtained, the configuration from which the components are deleted can be extracted as the invention.

According to the present invention described above, the ultrasound vibration for removal of adhering extraneous matters can be efficiently propagated from the transducer into the observation field of view region in the observation window, and the endoscope apparatus which can reliably remove the adhering extraneous matters on the observation window can be realized.

What is claimed is:

1. An endoscope apparatus, comprising:
  a transparent member that is provided at a distal end of an insertion portion of an endoscope and opposed to an image pickup optical system;
  a transducer that is attached to an inner surface of the transparent member;
  a diffraction grating that is provided on an outer surface of the transparent member, and converts an ultrasound vibration from the transducer into a surface acoustic wave which propagates on the outer surface of the transparent member; and
  an absorption portion that is provided at an outer peripheral portion of the transparent member, and deflects the propagated surface acoustic wave to a surface different from the outer surface to absorb the surface acoustic wave,
  wherein the transparent member has a first region, which absorbs the surface acoustic wave and a second region which reflects the surface acoustic wave, at an outline portion to be an outer surface contour, the first region is a region which the surface acoustic wave reaches by being propagated onto the outer surface in a direction of an observation field of view from the diffraction grating, and the second region is a region which the surface acoustic wave reaches by being propagated onto the outer surface in a direction opposite from the direction of the observation field of view from the diffraction grating, and wherein in the second region of the transparent member, a reflection surface is formed, which reflects the surface acoustic wave, which reaches the reflection surface by being propagated onto the outer surface, in a direction opposite from an incident direction.

2. The endoscope apparatus according to claim 1, wherein in the transparent member, the reflection surface which reflects the surface acoustic wave is formed by a part of the outline portion being chamfered, and a side surface portion including the reflection surface is in surface contact with and fixed to a fixed support member provided at the insertion portion.

3. The endoscope apparatus according to claim 1, wherein in the transparent member, an angle formed by the outer surface and the reflection surface is substantially 90 degrees.

4. An endoscope apparatus, comprising:
a transparent member that is provided at a distal end of an insertion portion of an endoscope and opposed to an image pickup optical system;
a transducer that is attached to an inner surface of the transparent member;
a diffraction grating that is provided on an outer surface of the transparent member, and converts an ultrasound vibration from the transducer into a surface acoustic wave which propagates on the outer surface of the transparent member; and
an absorption portion that is provided at an outer peripheral portion of the transparent member, and deflects the propagated surface acoustic wave to a surface different from the outer surface to absorb the surface acoustic wave,
wherein in the transparent member, a fixed support member provided at the distal end of the insertion portion and a side surface portion are in surface contact with and fixed to each other.

5. The endoscope apparatus according to claim 4, wherein in the reflection surface, only a surface which extends to the inner surface side from a position having a distance of one wavelength of the surface acoustic wave or more to the inner surface side from the outer surface is in surface contact with and fixed to the fixed support member.

* * * * *